United States Patent
Missling

(10) Patent No.: US 12,144,819 B2
(45) Date of Patent: *Nov. 19, 2024

(54) PHARMACEUTICAL COMPOSITION AND USE

(71) Applicant: SpineThera, Plymouth, MN (US)

(72) Inventor: Jeffrey Missling, Eden Prairie, MN (US)

(73) Assignee: SPINETHERA, Plymouth, MN (US)

( * ) Notice: Subject to any disclaimer, the term of this patent is extended or adjusted under 35 U.S.C. 154(b) by 338 days.

This patent is subject to a terminal disclaimer.

(21) Appl. No.: 17/348,471

(22) Filed: Jun. 15, 2021

(65) Prior Publication Data

US 2021/0379083 A1  Dec. 9, 2021

Related U.S. Application Data

(63) Continuation of application No. 16/437,201, filed on Jun. 11, 2019, now Pat. No. 11,058,692, which is a continuation of application No. 15/421,003, filed on Jan. 31, 2017, now Pat. No. 10,350,222, which is a continuation of application No. 14/561,797, filed on Dec. 5, 2014, now Pat. No. 9,572,771, which is a continuation of application No. 13/752,931, filed on Jan. 29, 2013, now Pat. No. 8,927,529.

(60) Provisional application No. 61/592,438, filed on Jan. 30, 2012.

(51) Int. Cl.
| | |
|---|---|
| *A61K 31/573* | (2006.01) |
| *A61K 9/00* | (2006.01) |
| *A61K 9/14* | (2006.01) |
| *A61K 9/16* | (2006.01) |
| *A61K 9/50* | (2006.01) |
| *A61K 47/10* | (2017.01) |
| *A61K 47/34* | (2017.01) |

(52) U.S. Cl.
CPC .......... *A61K 31/573* (2013.01); *A61K 9/0019* (2013.01); *A61K 9/0085* (2013.01); *A61K 9/146* (2013.01); *A61K 9/16* (2013.01); *A61K 9/1647* (2013.01); *A61K 9/5031* (2013.01); *A61K 47/10* (2013.01); *A61K 47/34* (2013.01); *A61K 9/0051* (2013.01)

(58) Field of Classification Search
None
See application file for complete search history.

(56) References Cited

U.S. PATENT DOCUMENTS

| | | | |
|---|---|---|---|
| 5,565,215 | A  | 10/1996 | Gref et al. |
| 6,497,729 | B1 | 12/2002 | Moussy et al. |
| 7,758,778 | B2 | 7/2010  | Persyn et al. |
| 8,927,529 | B2 | 1/2015  | Missling et al. |
| 9,572,771 | B2 | 2/2017  | Missling et al. |
| 10,350,222 | B2 | 7/2019  | Missling et al. |
| 11,058,692 | B2 | 7/2021  | Missling |
| 2001/0012522 | A1 | 8/2001  | Ottoboni et al. |
| 2003/0099682 | A1 | 5/2003  | Moussy et al. |
| 2011/0206773 | A1 | 8/2011  | Lavik et al. |
| 2011/0212136 | A1 | 9/2011  | Osterhout et al. |
| 2011/0268808 | A1 | 11/2011 | Jain et al. |
| 2012/0282298 | A1 | 11/2012 | Bodick et al. |
| 2013/0195933 | A1 | 8/2013  | Missling |
| 2015/0087625 | A1 | 3/2015  | Missling |
| 2017/0136037 | A1 | 5/2017  | Missling |
| 2019/0290660 | A1 | 9/2019  | Missling |

OTHER PUBLICATIONS

"U.S. Appl. No. 13/752,931, Non Final Office Action mailed Apr. 15, 2014", 15 pgs.
"U.S. Appl. No. 13/752,931, Notice of Allowance mailed Sep. 26, 2014", 12 pgs.
"U.S. Appl. No. 13/752,931, Response filed Jun. 11, 2014 to Non Final Office Action mailed Apr. 15, 2014", 15 pgs.
"U.S. Appl. No. 14/561,797, Non Final Office Action mailed Mar. 15, 2016", 17 pgs.
"U.S. Appl. No. 14/561,797, Notice of Allowance mailed Oct. 17, 2016", Examiner Interview Summary from Oct. 17, 2016 included, 11 pgs.
"U.S. Appl. No. 14/561,797, Preliminary Amendment filed Dec. 30, 2014", 5 pgs.
"U.S. Appl. No. 14/561,797, Response filed Feb. 18, 2016 to Restriction Requirement mailed Dec. 18, 2015", 6 pgs.
"U.S. Appl. No. 14/561,797, Response filed Jul. 13, 2016 to Non-Final Office Action mailed Mar. 15, 2016", 11 pgs.
"U.S. Appl. No. 14/561,797, Restriction Requirement mailed Dec. 18, 2015", 6 pgs.
"U.S. Appl. No. 15/421,003, Examiner Interview Summary mailed Mar. 14, 2019", 3 pgs.
"U.S. Appl. No. 15/421,003, Examiner Interview Summary mailed Nov. 14, 2018", 3 pgs.
"U.S. Appl. No. 15/421,003, Final Office Action mailed Feb. 21, 2019", 12 pgs.
"U.S. Appl. No. 15/421,003, Non Final Office Action mailed Jun. 20, 2018", 12 pgs.
"U.S. Appl. No. 15/421,003, Notice of Allowance mailed May 8, 2019", 12 pgs.
"U.S. Appl. No. 15/421,003, Preliminary Amendment filed Feb. 15, 2017", 8 pgs.
"U.S. Appl. No. 15/421,003, Response filed Mar. 21, 2018 to Restriction Requirement mailed Feb. 22, 2018", 6 pgs.
"U.S. Appl. No. 15/421,003, Response filed Apr. 22, 2019 to Final Office Action mailed Feb. 21, 2019", 10 pgs.

(Continued)

*Primary Examiner* — Bethany P Barham
*Assistant Examiner* — Barbara S Frazier
(74) *Attorney, Agent, or Firm* — SCHWEGMAN LUNDBERG & WOESSNER, P.A.

(57) ABSTRACT

An injectable, flowable composition, kits that include the same, and methods of medical treatment of a mammal (e.g., human) that include the administration of the same are provided.

16 Claims, No Drawings

(56) References Cited

OTHER PUBLICATIONS

"U.S. Appl. No. 15/421,003, Response filed Nov. 20, 2018 to Non Final Office Action mailed Jun. 20, 2018", 8 pgs.
"U.S. Appl. No. 15/421,003, Restriction Requirement mailed Feb. 22, 2018", 10 pgs.
"U.S. Appl. No. 16/437,201, Examiner Interview Summary mailed Feb. 8, 2021", 2 pgs.
"U.S. Appl. No. 16/437,201, Examiner Interview Summary mailed Nov. 20, 2020", 2 pgs.
"U.S. Appl. No. 16/437,201, Non Final Office Action mailed Jun. 26, 2020", 15 pgs.
"U.S. Appl. No. 16/437,201, Notice of Allowance mailed Mar. 11, 2021", 8 pgs.
"U.S. Appl. No. 16/437,201, Preliminary Amendment filed Jun. 20, 2019", 8 pgs.
"U.S. Appl. No. 16/437,201, Response filed Dec. 8, 2020 to Non Final Office Action mailed Jun. 26, 2020", 12 pgs.
"Definition: Dexamthasone Acetate", USP Dictionary, (2011), 273-274.
"Dexamethasone Acetate", Merck Index, 14th Edition, (2006), p. 500.
Bodick, Neil, et al., "Corticosteroids for the Treatment of Joint Pain", U.S. Appl. No. 61/370,666 filed Aug. 4, 2010, 43 pgs.
Cohen, S. P, et al., "Randomized, double-blind, placebo-controlled, dose-response, and preclinical safety study of transforaminal epidural etanercept for the treatment of sciatica.", Anesthesiology, 110(5), (May 2009), 1116-26.
Hogan, Q. H, "Lumbar epidural anatomy. A new look by cryomicrotome section", Anesthesiology, 75(5), (Nov., 1991), 767-75.
James, Hector E, et al., "Effects of steroids on behavior, electrophysiology, water content and intracranial pressure in cerebral cytotoxic edema.", Pharmacol Biochem Behav., 9(5), (Nov., 1978), 653-7.
Rathmell, J P, et al., "Identification of the epidural space with optical spectroscopy: an in vivo swine study", Anesthesiology, 113(6), (Dec., 2010), 1406-18.

PHARMACEUTICAL COMPOSITION AND USE

CROSS REFERENCE TO RELATED APPLICATIONS

This application is a continuation of U.S. application Ser. No. 16/437,201, filed Jun. 11, 2019, entitled "PHARMACEUTICAL COMPOSITION AND USE", which is a continuation of U.S. application Ser. No. 15/421,003, filed Jan. 31, 2017, entitled "PHARMACEUTICAL COMPOSITION AND USE", which is a continuation of U.S. application Ser. No. 14/561,797, filed Dec. 5, 2014, entitled "PHARMACEUTICAL COMPOSITION AND USE," which application is a continuation of U.S. application Ser. No. 13/752,931, filed Jan. 29, 2013, entitled, "PHARMACEUTICAL COMPOSITION AND USE", which application claims the benefit of priority of U.S. Provisional Patent Application Ser. No. 61/592,438, entitled "PHARMACEUTICAL COMPOSITION AND USE," filed on Jan. 30, 2012, which application is incorporated by reference herein in its entirety.

BACKGROUND

Patients with low back pain and related discomforts (e.g., sciatica) are often treated with steroid suspensions or solutions that are injected into the epidural space. Methylprednisolone and dexamethasone are two steroids commonly used in this practice. Over 3 million epidural steroid injections are given annually in the United States to treat low back pain. The steroids methylprednisolone, dexamethasone, and betamethasone are not currently approved by the Food and Drug Agency (FDA) for this use, and the procedure is commonly requires fluoroscopy to guide the injection into a targeted space. It is not uncommon for patients to receive two or three injections over the period of several months, which not only increases the risk of medical complications, but can also be costly, inconvenient, and time-consuming.

SUMMARY

The present invention provides an injectable, flowable composition that includes: (a) microparticles that include an active pharmaceutical ingredient and a polymer, wherein the surface of the microparticles are hydrophilic; and (b) a hydrophilic, liquid carrier vehicle; wherein the microparticles are substantially miscible to dispersible in the liquid carrier vehicle.

The present invention also provides an injectable, flowable composition that includes: (a) microparticles that include an active pharmaceutical ingredient and a polymer, wherein the surface of the microparticles are hydrophobic; and (b) a hydrophobic, liquid carrier vehicle; wherein the microparticles are substantially miscible to dispersible in the liquid carrier vehicle.

The present invention also provides a kit that includes: (a) a first package (e.g., vial) that include microparticles that include an active pharmaceutical ingredient and a polymer, wherein the surface of the microparticles are hydrophilic; (b) a second package (e.g., vial) comprising a hydrophilic, liquid carrier vehicle; and (c) instructions or printed indicia; wherein the microparticles are substantially miscible to dispersible in the liquid carrier vehicle.

The present invention also provides a kit that includes: (a) a first package (e.g., vial) that include microparticles that include an active pharmaceutical ingredient and a polymer, wherein the surface of the microparticles are hydrophobic; (b) a second package (e.g., vial) comprising a hydrophobic, liquid carrier vehicle; and (c) instructions or printed indicia; wherein the microparticles are substantially miscible to dispersible in the liquid carrier vehicle.

The present invention also provides a method that includes administering to a mammal (e.g., human), via injection, an injectable, flowable composition described herein.

The present invention also provides a method for the treatment of a medical condition or disorder (e.g., back pain). The method includes injecting the injectable, flowable composition into lipophilic tissue (e.g., epidural space). The composition includes: (a) microparticles that include an active pharmaceutical ingredient and a polymer, wherein the surface of the microparticles are hydrophilic; and (b) a hydrophilic, liquid carrier vehicle. The microparticles are substantially miscible to dispersible in the liquid carrier vehicle.

The present invention also provides a method for the treatment of a medical condition or disorder (e.g., macular degeneration or diabetic macular edema). The method includes injecting the injectable, flowable composition into lipophobic tissue (e.g., intravitreal space of an eye). The composition includes: (a) microparticles that include an active pharmaceutical ingredient and a polymer, wherein the surface of the microparticles are hydrophobic; and (b) a hydrophobic, liquid carrier vehicle. The microparticles are substantially miscible to dispersible in the liquid carrier vehicle.

Advantages of the invention include the stabilization and localization of pharmaceutical agents in a targeted injection area for prolonged release of a pharmacological agent. In such embodiments, the injected volume remains localized in tissue. Spreading is diminished and delivery of the agent to the target site is increased, and active agent exposure to unintended locations is diminished.

Advantages of the invention include the reduction of the risk of infarct or other adverse side-effects when the delivery vehicle is an aqueous solution, if the practitioner injects the pharmaceutical composition outside the targeted injection site, e.g., into a blood vessel. For example, the compositions described herein are relatively effective and safe for accidental or intentional arterial administration. In specific embodiments, the microparticle surface properties (hydrophilic) avoids agglomeration. In additional embodiments, the particle size is small enough to pass through capillaries. In additional embodiments, the hydrophilic surface particle and/or release of anti-inflammatory agent reduces the occurrence of an inflammatory response typically encountered with small diameter sized particles.

Advantages of the invention include the reduction of cost and inconvenience to both the patient and health insurance agencies associated with repeated therapeutic injections into the same area.

Advantages of the invention include the reduction of damaging effects on the liver and other bodily filters in processing excess pharmaceutical agents that are removed from the targeted injection site when using conventional injection techniques.

Advantages of the invention include the use of a microparticle/delivery vehicle suspension that has a high degree of stability, thus providing the capability to perform accurate dosing without placing impractical or inconvenient limits of the time between mixing and loading the delivery device on the practitioner. For example, the compositions herein in specific embodiments include a stable suspension (decreased settling) upon reconstitution (addition of diluent to microparticles), which can lead to more accurate dosing.

Advantages of the invention include, in specific embodiments, the selection of a poorly water-soluble and highly potent active agent. This can decrease the exposure of the active agent to excipients. This can also facilitate long duration or sustained release of the active agent.

Advantages of the invention include, in specific embodiments, the selection dexamethasone (or dexamethasone acetate) as the active agent. This specific active agent does not reduce or dehydrate neural tissue to any significant or appreciable degree.

DETAILED DESCRIPTION

Reference will now be made in detail to certain claims of the invention, examples of which are illustrated herein. While the presently disclosed subject matter will be described in conjunction with the enumerated claims, it will be understood that the invention as described by the disclosed subject matter does not limit the claims. On the contrary, the disclosed subject matter is intended to cover all alternatives, modifications, and equivalents, which may be included within the scope of the invention as defined by the claims.

References in the specification to "one embodiment", "specific embodiments", "an example embodiment", etc., indicate that the embodiment described may include a particular feature, structure, or characteristic, but every embodiment may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The presently disclosed subject matter relates to injectable, flowable compositions, methods of manufacturing the same, kits that include the same, and methods of medical treatment that include administering the same.

Injectable, Flowable Composition

In specific embodiments, the injectable, flowable composition includes: (a) microparticles that include an active pharmaceutical ingredient and a polymer, wherein the surface of the microparticles are hydrophilic; and (b) a hydrophilic, liquid carrier vehicle; wherein the microparticles are substantially miscible to dispersible in the liquid carrier vehicle. In alternative specific embodiments, the injectable, flowable composition includes: (a) microparticles that include an active pharmaceutical ingredient and a polymer, wherein the surface of the microparticles are hydrophobic; and (b) a hydrophobic, liquid carrier vehicle; wherein the microparticles are substantially miscible to dispersible in the liquid carrier vehicle.

The hydrophilic, liquid carrier vehicle can include substances that are suitable and appropriate for use as a liquid vehicle carrier. In specific embodiments, the hydrophilic, liquid carrier vehicle can include water.

The hydrophobic, liquid carrier vehicle can include substances that are suitable and appropriate for use as a liquid vehicle carrier. For example, the hydrophobic, liquid carrier vehicle can include at least one of an oil derived from a plant, an oil derived from a silicone-containing oil, and a microbial/biological/biotechnology/fermentation/metabolic activity.

The injectable, flowable composition can be formulated to provide a desired or requisite rate of release of the API. In specific embodiments, the injectable, flowable composition can be formulated to provide a sustained release of API. In additional specific embodiments, the injectable, flowable composition can be formulated to provide an immediate release of API. In additional specific embodiments, the injectable, flowable composition can be formulated to provide an extended release of API. In additional specific embodiments, the injectable, flowable composition can be formulated to provide a modified release of API. In additional specific embodiments, the injectable, flowable composition can be formulated to provide a combination (or mixture or hybrid) release of API, described above.

The injectable, flowable composition can have any suitable and appropriate pH. In specific embodiments, the injectable, flowable composition can have a pH of less than about 8.5. In additional specific embodiments, the injectable, flowable composition can have a pH of about 7.0 to about 8.5.

In specific embodiments, the injectable, flowable composition can include a buffer. The inclusion of a buffer can depend on the chemistry or environmental factors (pH, etc.) of the intended target physiology. See, e.g., U.S. application Ser. No. 13/143,884.

The injectable, flowable composition can have any suitable and appropriate volume. In specific embodiments, it may be desirable to employ an injectable, flowable composition having a relatively low volume, for patient safety, compliance, and comfort purposes. As such, in specific embodiments, the injectable, flowable composition can have a total volume of less than about 50 mL. In additional specific embodiments, the injectable, flowable composition can have a total volume of less than about 20 mL. In additional specific embodiments, the injectable, flowable composition can have a total volume of less than about 5 mL. In additional specific embodiments, the injectable, flowable composition can have a total volume of less than about 1 mL.

Microparticles

The present invention provides an injectable, flowable composition that includes microparticles and a liquid carrier vehicle. The microparticles include an active pharmaceutical ingredient and a polymer. The surface of the microparticles are either hydrophilic or hydrophobic. The microparticles are substantially miscible to dispersible in the liquid carrier vehicle.

The microparticles include an active pharmaceutical ingredient and polymer. The core of the microparticles can include an API (e.g., dexamethasone acetate), which has relatively poor water-solubility, and polymer (e.g., polylactide-co-gylocide (PLGA)); and the surface of the microparticle can be functionalized with a polymer (e.g., PLGA-co-polyethylene-glycol block copolymer, wherein the PEG block is distal to the surface of the microparticle). The surface of the microparticle can also include a specified amount of API, the amount of which may be optimized to control burst release of the drug. U.S. Pat. No. 7,758,778 describes methods for preparing microparticle formulations containing pharmaceutically active agents.

The surface of the microparticles can be selected or modified through functionalization to serve at least two purposes: first, to be soluble or miscible in the delivery vehicle, and second, to be insoluble or immiscible in the targeted physiological injection site. In general, microparticles incorporating pharmaceutical or pharmacological agents—and surface modification of the particles—can be prepared by methods known in the art. See, for example, U.S. patent application Ser. No. 10/066,393, filed Jan. 31, 2002, and U.S. Pat. No. 6,497,729. Other suitable synthetic methods known in the art can be employed.

The selection and/or modification through functionalization of the surface of the microparticles provides a stable, homogeneous injection solution or suspension (to include the delivery vehicle and the microparticles), minimizes precipitation or settling of the microparticles, improves performance when administering the injection solution, and allows a practitioner to reliably administer an effective dose of the pharmacological agent. At the same time, the immiscibility between the injection solution or suspension and the targeted physiological injection site provides the capability for the microparticles to agglomerate at the injection site as described herein.

As such, the microparticles can include surface moieties selected to provide a desired miscibility or solubility for a given application as described herein; i.e., the microparticles can have a desired hydrophilicity, hydrophobicity, lipophilicity, lipophobicity, or other desired miscibility or solubility characteristic. In one embodiment, the microparticles can include surface moieties selected to maximize miscibility or solubility within an injection vehicle, while at the same time minimizing miscibility or solubility within a targeted physiological environment. Specifically, the microparticles will be substantially miscible or dispersible in the carrier vehicle, wherein the microparticles and the carrier vehicle will be substantially insoluble or immiscible in the targeted anatomical injection site of the patient.

In specific embodiments, the microparticle surface includes a substantially polar, water-miscible, or water-soluble material. In alternative specific embodiments, the microparticle surface includes a substantially non-polar, water-immiscible, or water-insoluble material.

In specific embodiments, an aqueous-miscible (i.e., a hydrophilic) microparticle can be prepared by functionalizing the microparticle surface with an amphiphilic block copolymer. The block copolymer can include a hydrophobic block and a hydrophilic block, where the hydrophilic block is distal to the microparticle surface (i.e., the block copolymer is oriented with the hydrophilic block furthest from the microparticle surface). See, e.g., U.S. Pat. No. 5,565,215, filed Mar. 18, 1994.

In specific embodiments, an aqueous-miscible (i.e., a hydrophilic) microparticle can be prepared by coating a hydrophobic microparticle with a hydrophilic surface moiety, such as a polysaccharide, hylaranounic acid, or poly(ethylene glycol) (PEG). See, e.g., U.S. application Ser. No. 13/143,884, filed Jan. 8, 2010. The process of microparticle surface coating may be done by methods known in the art, including grafting or linking methods.

In specific embodiments, a water-immiscible microparticle (e.g., a microparticle having a substantially hydrophobic surface) can be prepared by the incorporation of a homopolymer or copolymer containing hydrophobic blocks, for example poly(lactide), poly(glycolide), poly(caprolactone), poly(valerolactone), poly(hydroxybutyrate), and copolymers thereof.

In general, and without wishing to be bound by theory, it is believed that when a carrier vehicle (e.g., an aqueous phase) containing suspended microparticles is injected into a biological environment having substantially different hydrophilicity or hydrophobicity than the suspension or solution itself, the carrier vehicle will form a separate phase with respect to the environment (similar to injecting oil into water). Over time, the carrier vehicle will be absorbed by the body, while the microparticles will remain substantially localized at the injection site. Eventually, the carrier vehicle will be substantially absorbed by the body, leaving a localized, agglomerated concentration of the microparticles at or substantially near the injection area. As the microparticles degrade over time, and through diffusion processes, the pharmacological agent(s) contained therein can be released into the immediate anatomical surroundings, providing localized delivery of the therapeutic agent.

As is described in the art, accidental injection of a pharmacological agent into an unintended anatomy can pose serious health risks for the patient. Injection of particulate matter into an artery can result in blocking or obstruction of the artery, resulting in damage to tissue relying on the blood supplied by the blocked artery. This is particularly true for biodegradable microparticles having a size dimension greater than about 10 microns, since the microparticles cannot pass easily through capillary beds. As such, in specific embodiments, the microparticles described herein will have a size of about 10 microns or less.

In general, the pharmaceutical compositions and methods described herein can reduce the likelihood of infarct if a practitioner accidently injects the pharmaceutical composition into a vein or artery. This advantage is provided by at least two features of the pharmaceutical composition: first, in some embodiments, the pharmaceutical composition can include microparticles having an average size of about 10 microns (μm) or less. This size range is believed to allow microparticles that are accidently introduced into a blood supply to pass through the capillary bed without causing obstruction. See, e.g., U.S. patent application Ser. No. 09/758,988, filed Jan. 11, 2001. Second, in embodiments where the biodegradable microparticles are hydrophilic, or have been surface-functionalized to be hydrophilic, they will be substantially miscible or soluble with blood. Thus, the risk of spinal cord infarct resulting from accidental injection outside of the target injection area (i.e., the epidural space), or into arteries that pass through the epidural space can be reduced.

The microparticles employed herein will have a suitable and appropriate dimension. For example, the microparticles can be oval, spherical, elliptical, tubular, etc. In additional to the shape, the microparticles will have a suitable size. For example, the microparticles can have a $d_{50}$ of less than about 5 μm. Specifically, the microparticles can have a $d_{50}$ of about 2 μm to about 5 μm. Additionally, the microparticles can have a $d_{90}$ of less than about 7 μm. Specifically, the microparticles can have a $d_{90}$ of less than about 5 μm.

In specific embodiments, the microparticles are biodegradable. In additional specific embodiments, the microparticles are bioerodible. In additional specific embodiments, the microparticles are biocompatible.

The microparticles can be present in any suitable and appropriate concentration, in the injectable, flowable composition. In specific embodiments, the microparticles can be present in a concentration of about 1 mg/ml to about 500 mg/ml of the liquid carrier vehicle.

API

Any suitable active pharmaceutical ingredient (API) can be employed herein, provided the resulting injectable, flowable composition retains its chemical and physical stability, as well as requisite biological activity, over the extended periods of time associated with the manufacture, shipping and storage of the product. Suitable APIs are disclosed, for example, in the Merck Index (14$^{th}$ Ed.) and the USP Dictionary (2011). The selection of specific (or class) of API will typically depend, e.g., on the underlying disease or disorder to be treated.

One specific class of APIs that can be employed includes anti-inflammatory agents, for example, synthetic, glucocorticoid steroids. Within the synthetic, glucocorticoid steroids, a specific API that can be employed is dexamethasone acetate, 9 alpha-fluoro-11-beta, 17-alpha, 21-trihydroxy-16 alpha-methylpregna-1,4-diene-3,20-dione 21-acetate.

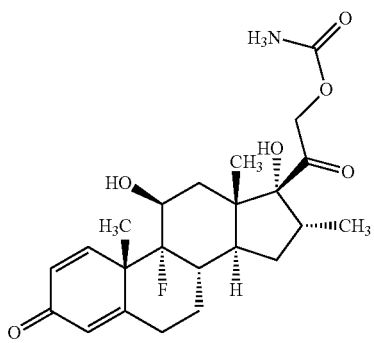

Use of dexamethasone acetate as an anti-inflammatory agent can be advantageous in specific embodiments. Dexamethasone acetate has a relatively low water-solubility, which facilitates sustained drug delivery from the biodegradable microparticles. Additionally, the drug has been shown to be a relatively potent corticosteroid that does not reduce water content of neural tissue.

Dexamethasone acetate has higher anti-inflammatory potency than many other corticosteroids, which may reduce the number of doses needed to treat the patient. Dexamethasone acetate also has low water solubility, <0.15 mg/mL, which can be preferred for formulation of a sustained-release dosage form. As diffusion and polymer degradation are two main mechanisms of drug release from biodegradable microparticles, a pharmacological agent having lower water solubility may elute at a slower rate from the microparticles compared to other agents with high water solubility. Furthermore, dexamethasone acetate has been shown to achieve an anti-inflammatory effect in the brain without reducing tissue water content. See, e.g., H. James, "Effects of Steroids on Behavior, Electrophysiology, Water Content and Intracranial Pressure in Cerebral Cytotoxic Edema," Pharmacology Biochemistry and Behavior, Vol. 9, pp. 653-657, 1978. Thus, in specific embodiments, it can be advantageous to choose dexamethasone acetate for treatment of low back pain to avoid reduction in water content of the targeted nerve roots.

Selection of the API will depend in part upon the underlying disease or disorder to be treated. For example, the composition described herein, including the API, can be administered via an intravitreal injection into the eye. For such an administration, the composition can be employed to treat, e.g., macular degeneration or diabetic macular edema. APIs suitable for the treatment of such diseases or disorders are disclosed, e.g., in the Merck Index (14th Ed.) and the USP Dictionary (2011). For example, in embodiments where the composition is employed to treat diabetic macular edema, via an intravitreal injection into the eye, the API can include dexamethasone acetate.

The API can be present in the injectable, flowable composition in any suitable and appropriate amount. For example, the API can be present in the injectable, flowable composition in an amount such that the resulting injectable, flowable composition retains its chemical and physical stability, as well as requisite biological activity, over the extended periods of time associated with the manufacture, shipping and storage of the product.

In specific embodiments, it may be desirable to maximize, or increase, the amount of API present, relative to the total amount of injectable, flowable composition. In such embodiments, it may be desirable to employ an injectable, flowable composition having a relatively low volume, for patient safety, compliance, and comfort purposes.

As such, in specific embodiments, the active pharmaceutical ingredient can be present in a weight of up to about 40% the weight of the polymer. In further specific embodiments, the active pharmaceutical ingredient can be present in a weight of up to about 30% the weight of the polymer. In alternative specific embodiments, the active pharmaceutical ingredient can be present in a weight of at least about 10% the weight of the polymer. In further specific embodiments, the active pharmaceutical ingredient can be present in a weight of at least about 20% the weight of the polymer. In alternative specific embodiments, the active pharmaceutical ingredient can be present in a weight of about 20-30% the weight of the polymer.

The specific amount (measured in units of mass) of API employed in the injectable, flowable composition will typically depend, for example, on the amount of composition to be delivered. The amount of composition to be delivered will typically depend, for example, on the size, weight, age and health condition of the patient, the disease or disorder to be treated, the location or site of administration, as well as the specific API employed.

Polymer

In specific embodiments, the polymer can include an amphiphilic block copolymer. In additional specific embodiments, the polymer can include a copolymer of lactic acid and glycolic acid (e.g., PLGA). In additional specific embodiments, the polymer can include at least one of PLGA-block-PEG and PLGA.

In specific embodiments, the surface of the microparticles can be hydrophilic. In such embodiments, the liquid carrier vehicle can be hydrophilic, and the polymer can include a PLGA core and a PLGA-block-PEG surface. Additionally, in specific embodiments wherein the surface of the microparticles are hydrophilic and the liquid carrier vehicle is hydrophilic, the resulting injectable, flowable composition can be configured for injection into a hydrophobic environment (e.g., fatty tissue, an epidural space, etc.).

Alternatively, in specific embodiments, the surface of the microparticles can be hydrophobic. In such embodiments, the liquid carrier vehicle can be hydrophobic, and the polymer can include PLGA. Additionally, in specific embodiments wherein the surface of the microparticles are hydrophobic, and the liquid carrier vehicle is hydrophobic, then the injectable, flowable composition can be configured for injection into a hydrophilic environment (e.g., an eye, or surrounding tissue, the vitreous body of an eye, or surrounding tissue, a joint, the synovial cavity of a joint, etc.).

In specific embodiments, the PLGA can be poly(D,L-lactide-co-glycolide). In additional specific embodiments, PLGA can be poly(D,L-lactide-co-glycolide) [50:50 to 95:5].

In specific embodiments, the PLGA-block-PEG surface can be poly(D,L-lactide-co-glycolide)-co-polyethylene glycol. In additional specific embodiments, the PLGA-block-PEG surface can be poly(D,L-lactide-co-glycolide) [50:50 to 95:5]-co-polyethylene glycol. In additional specific embodiments, the PLGA-block-PEG surface can be poly(D, L-lactide-co-glycolide)[85:15]-co-polyethylene glycol.

The PEG portion of the PLGA-block-PEG polymer can have a suitable and appropriate molecular weight range. For example, in specific embodiments, the PEG portion of the PLGA-block-PEG polymer can have a molecular weight of up to 10,000 daltons. In additional specific embodiments, the PEG portion of the PLGA-block-PEG polymer can have a molecular weight of about 2kD.

Kits

The kit can include all of the desired tools, solutions, compounds, including mixing vessels, utensils, and injection devices, to treat a patient according to any of the methods described herein. In one embodiment, a kit includes pharmaceutically-active biodegradable microparticles of the type described herein. The microparticles can be sterile-packaged as a dry powder in a substantially water-impermeable container. The kit can also include an injection vehicle such as sterile water (in the case where the target injection area is substantially hydrophobic or lipophilic) or other suitable vehicle. Prior to administration, the biodegradable microparticles can be added to the injection vehicle to form a suspension and agitated (e.g., stirred or shaken) to maximize homogeneity. The kit can further include a hypodermic needle or other delivery device. The kit can further include instructions, dosage tables, and other pertinent information for the practitioner.

The kits will include instructions or printed indicia, to provide for directions for reconstituting the contents of the multiple packages, and/or for the administration of the resulting composition (e.g., the injectable, flowable composition). In specific embodiments, the instructions on printed indicia will instruct injection into at least one of fatty tissue, hydrophobic tissue, and epidural tissue. In additional specific embodiments, the instructions on printed indicia will instruct injection into at least one of hydrophilic tissues, an eye, and vitreous.

Methods for Use (Medical Treatment)

The microparticles described herein can be stored, e.g., as a lyophilized powder in a sealed, dry container. Prior to injection, the particles can be mixed with an injection vehicle, and an aliquot of the resulting suspension can be collected for injection into the patient. In typical settings, this procedure can be done by drawing the suspension into a hypodermic needle for subcutaneous injection. However, other methods of delivering the suspension to a desired injection are can be used. In one embodiment, a 22 gauge, 3.5 inch Quincke spinal needle can be used. In another embodiment, a Touhy needle can be used. Other methods will be apparent to those skilled in the art. See, e.g., Cohen et al, "Randomized, Double-blind, Placebo-controlled, Dose Response, and Preclinical Safety Study of Transforaminal Epidural Etanercept for the treatment of Sciatica," Anesthesiology, Vol. 110, pp. 1116-1126 (2009).

One problem with existing microparticle formulations is settling of the microparticles in the delivery vehicle, which can affect patient dosing. A uniform, but unstable suspension of biodegradable microparticles can be achieved, in prior art systems and methods, by mixing or stirring the microparticles into the delivery vehicle. It then becomes necessary, in most cases, to immediately load the suspension into the delivery device (e.g. a hypodermic needle) immediately after mixing since the microparticles will begin to settle after a period of time. The concentration of microparticles in the suspension can vary using this type of approach, since the amount of time between mixing, needle loading, and injection depend on the practitioner-dependent variables.

In contrast, advantages of the invention include the use of a microparticle/delivery vehicle suspension that has a high degree of stability, thus providing the capability to perform accurate dosing without placing impractical or inconvenient limits of the time between mixing and loading the delivery device on the practitioner.

The injectable, flowable compositions described herein can be formulated for administration, via injection, to a mammal (e.g., human).

As described herein, the injectable, flowable composition can be formulated to provide a desired or requisite rate of release of the API. In specific embodiments, the injectable, flowable composition can have a substantially first order release profile. In alternative specific embodiments, the injectable, flowable composition can have a substantially zero order release profile.

As stated herein, in specific embodiments, the surface of the microparticles can be hydrophilic. In such embodiments, the liquid carrier vehicle can be hydrophilic, and the polymer can include a PLGA core and a PLGA-block-PEG surface. Additionally, in specific embodiments wherein the surface of the microparticles are hydrophilic and the liquid carrier vehicle is hydrophilic, the resulting injectable, flowable composition can be injected into a hydrophobic environment (e.g., fatty tissue, an epidural space, etc.). A non-limiting example of a lipophilic region of a patient anatomy includes the epidural space. See, e.g., Rathmell, J. P. et al., "Identification of the Epidural Space with Optical Spectroscopy," Anesthesiology, Vol. 113(6), December, 2010, pp 1406-1418; and Hogan, Q. H., "Lumbar Epidural Anatomy," Anesthesiology, Vol. 75(5), November 1991, pp. 767-775.

As stated herein, in alternative specific embodiments, the surface of the microparticles can be hydrophobic. In such embodiments, the liquid carrier vehicle can be hydrophobic, and the polymer can include PLGA. Additionally, in specific embodiments wherein the surface of the microparticles are hydrophobic, and the liquid carrier vehicle is hydrophobic, then the injectable, flowable composition can be injected into a hydrophilic environment (e.g., an eye, or surrounding tissue, the vitreous body of an eye, or surrounding tissue, a joint, the synovial cavity of a joint, etc.).

As stated herein, the selection of specific (or class) of API will typically depend, e.g., on the underlying disease or disorder to be treated. In specific embodiments where the API is an anti-inflammatory agent, for example, a synthetic, glucocorticoid steroid, such as dexamethasone acetate, the disease or disorder to be treated can include at least one of: pain, chronic pain, mild pain, moderate pain, severe pain, acute pain, neuropathic pain, lower back pain, sciatica, radiculopathy, and lumbrosacral radiculopathy.

As stated herein, the flowable composition can be injected into a hydrophilic environment (e.g., an eye, or surrounding tissue, the vitreous body of an eye, or surrounding tissue, a joint, the synovial cavity of a joint, etc.), or can be injected into a hydrophobic environment (e.g., fatty tissue, an epidural space, etc.). As such, the injection can include intradermal as well as subcutaneous injections.

Depending upon the selection of polymer, microparticle, API, etc., the API can be released into the target injection site area over a specified period of time. For example, the polymer, microparticle, and API can independently be selected for release of the API into the target injection area over a period of days, weeks, or months. This process can occur by, e.g., diffusion of the API out of the microparticles; or by the microparticles dissolving or decomposing over time, which can release the API into the injection site. In one embodiment, the microparticles are capable of releasing the API over selectable periods ranging from about 2-24 weeks. Thus, a patient can receive substantially-continual dosing of the API over extended periods, if desired, which can reduce the need to receive repeated injection treatments.

The injectable, flowable compositions described herein can be formulated for administration, via injection, to a mammal (e.g., human), over a suitable, appropriate and effective period of time. In specific embodiments, the administration can be carried out no more than once per about 2 weeks. In additional specific embodiments, the administration can be carried out no more than once per about 6 weeks. In additional specific embodiments, the administration can be carried out no more than once per about 12 weeks. In additional specific embodiments, the administration can be carried out no more than once per about 18 weeks. In additional specific embodiments, the administration can be carried out no more than once per about 24 weeks.

In specific embodiments, the administration is carried out with fluoroscopy. In alternative specific embodiments, the administration is carried out without fluoroscopy.

Enumerated Embodiments

Specific enumerated embodiments [1] to [82] provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

[1.] An injectable, flowable composition comprising:
(a) microparticles comprising an active pharmaceutical ingredient and a polymer, wherein the surface of the microparticles are hydrophilic; and
(b) a hydrophilic, liquid carrier vehicle;
wherein the microparticles are substantially miscible to dispersible in the liquid carrier vehicle.

[2.] An injectable, flowable composition comprising:
(a) microparticles comprising an active pharmaceutical ingredient and a polymer, wherein the surface of the microparticles are hydrophobic; and
(b) a hydrophobic, liquid carrier vehicle;
wherein the microparticles are substantially miscible to dispersible in the liquid carrier vehicle.

[3.] The injectable, flowable composition of any of the above embodiments, wherein the microparticles have a $d_{50}$ of less than about 5 μm.

[4.] The injectable, flowable composition of any of the above embodiments, wherein the microparticles have a $d_{50}$ of about 2 μm to about 5 μm.

[5.] The injectable, flowable composition of any of the above embodiments, wherein the microparticles have a $d_{90}$ of less than about 7 μm.

[6.] The injectable, flowable composition of any of the above embodiments, wherein the microparticles have a $d_{90}$ of less than about 5 μm.

[7.] The injectable, flowable composition of any of the above embodiments, wherein the active pharmaceutical ingredient comprises an anti-inflammatory agent.

[8.] The injectable, flowable composition of any of the above embodiments, wherein the active pharmaceutical ingredient comprises a synthetic, glucocorticoid steroid.

[9.] The injectable, flowable composition of any of the above embodiments, wherein the active pharmaceutical ingredient comprises dexamethasone acetate, 9 alpha-fluoro-11-beta, 17-alpha, 21-trihydroxy-16 alpha-methyl-pregna-1,4-diene-3,20-dione 21-acetate

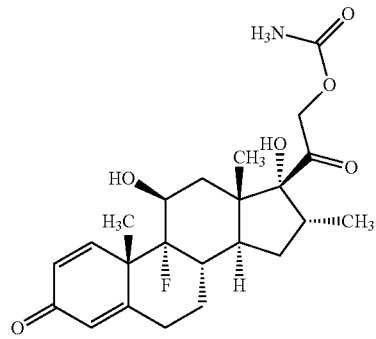

[10.] The injectable, flowable composition of any of the above embodiments, wherein the polymer comprises an amphiphilic block copolymer.

[11.] The injectable, flowable composition of any of the above embodiments, wherein the polymer is a copolymer of lactic acid and glycolic acid (PLGA).

[12.] The injectable, flowable composition of any of the above embodiments, wherein the polymer is a random or block copolymer of lactic acid and glycolic acid (PLGA).

[13.] The injectable, flowable composition of any of the above embodiments, wherein the polymer comprises at least one of PLGA-block-PEG and PLGA.

[14.] The injectable, flowable composition of any of the above embodiments, wherein when (i) the surface of the microparticles are hydrophilic, and (ii) the liquid carrier vehicle is hydrophilic, then the polymer comprises a PLGA core and a PLGA-block-PEG surface.

[15.] The injectable, flowable composition of any of the above embodiments, wherein when (i) the surface of the microparticles are hydrophobic, and (ii) the liquid carrier vehicle is hydrophobic, then the polymer comprises PLGA.

[16.] The injectable, flowable composition of any of the above embodiments, wherein the PLGA is poly(D,L-lactide-co-glycolide)[50:50 to 95:5].

[17.] The injectable, flowable composition of any of the above embodiments, wherein the PLGA-block-PEG surface is poly(D,L-lactide-co-glycolide)[50:50 to 95:5]-co-polyethylene glycol.

[18.] The injectable, flowable composition of any of the above embodiments, wherein the PLGA-block-PEG surface is poly(D,L-lactide-co-glycolide)[85:15]-co-polyethylene glycol.

[19.] The injectable, flowable composition of any of the above embodiments, wherein the PEG portion of the PLGA-block-PEG polymer has a molecular weight of up to 10,000 daltons.

[20.] The injectable, flowable composition of any of the above embodiments, wherein the PEG portion of the PLGA-block-PEG polymer has a molecular weight of about 2 kD.

[21.] The injectable, flowable composition of any of the above embodiments, wherein the microparticles are biodegradable.

[22.] The injectable, flowable composition of any of the above embodiments, wherein the microparticles are bioerodible.

[23.] The injectable, flowable composition of any of the above embodiments, wherein the microparticles are biocompatable.

[24.] The injectable, flowable composition of any of the above embodiments, wherein the active pharmaceutical ingredient is present in a weight of up to about 40% the weight of the polymer.

[25.] The injectable, flowable composition of any of the above embodiments, wherein the active pharmaceutical ingredient is present in a weight of up to about 30% the weight of the polymer.

[26.] The injectable, flowable composition of any of the above embodiments, wherein the active pharmaceutical ingredient is present in a weight of at least about 10% the weight of the polymer.

[27.] The injectable, flowable composition of any of the above embodiments, wherein the active pharmaceutical ingredient is present in a weight of at least about 20% the weight of the polymer.

[28.] The injectable, flowable composition of any of the above embodiments, wherein the active pharmaceutical ingredient is present in a weight of about 20-30% the weight of the polymer.

[29.] The injectable, flowable composition of any of the above embodiments, wherein when (i) the surface of the microparticles are hydrophilic, and (ii) the liquid carrier vehicle is hydrophilic, then the injectable, flowable composition is configured for injection into a hydrophobic environment.

[30.] The injectable, flowable composition of any of the above embodiments, wherein when (i) the surface of the microparticles are hydrophilic, and (ii) the liquid carrier vehicle is hydrophilic, then the injectable, flowable composition is configured for injection into fatty tissue.

[31.] The injectable, flowable composition of any of the above embodiments, wherein when (i) the surface of the microparticles are hydrophilic, and (ii) the liquid carrier vehicle is hydrophilic, then the injectable, flowable composition is configured for injection into an epidural space.

[32.] The injectable, flowable composition of any of the above embodiments, wherein when (i) the surface of the microparticles are hydrophobic, and (ii) the liquid carrier vehicle is hydrophobic, then the injectable, flowable composition is configured for injection into a hydrophilic environment.

[33.] The injectable, flowable composition of any of the above embodiments, wherein when (i) the surface of the microparticles are hydrophobic, and (ii) the liquid carrier vehicle is hydrophobic, then the injectable, flowable composition is configured for injection into an eye, or surrounding tissue.

[34.] The injectable, flowable composition of any of the above embodiments, wherein when (i) the surface of the microparticles are hydrophobic, and (ii) the liquid carrier vehicle is hydrophobic, then the injectable, flowable composition is configured for injection into the vitreous fluid of an eye.

[35.] The injectable, flowable composition of any of the above embodiments, wherein when (i) the surface of the microparticles are hydrophobic, and (ii) the liquid carrier vehicle is hydrophobic, then the injectable, flowable composition is configured for injection into the synovial cavity of a joint.

[36.] The injectable, flowable composition of any of the above embodiments, wherein the hydrophilic, liquid carrier vehicle comprises an aqueous liquid.

[37.] The injectable, flowable composition of any of the above embodiments, wherein the hydrophilic, liquid carrier vehicle comprises water.

[38.] The injectable, flowable composition of any of the above embodiments, wherein the hydrophobic, liquid carrier vehicle comprises at least one of an oil derived from a plant, an oil derived from a microbial/biological/biotechnology/fermentation/metabolic activity, and a silicone-containing oil.

[39.] The injectable, flowable composition of any of the above embodiments, which is a sustained release composition.

[40.] The injectable, flowable composition of any of the above embodiments, which is a controlled release composition.

[41.] The injectable, flowable composition of any of the above embodiments, which is a modified release composition.

[42.] The injectable, flowable composition of any of the above embodiments, wherein the microparticles are present in a concentration of about 1 mg/ml to about 500 mg/ml of the liquid carrier vehicle.

[43.] The injectable, flowable composition of any of the above embodiments, wherein the microparticles were previously lyophilized.

[44.] The injectable, flowable composition of any of the above embodiments, having a pH of less than about 8.5.

[45.] The injectable, flowable composition of any of the above embodiments, having a pH of about 7.0 to about 8.5.

[46.] The injectable, flowable composition of any of the above embodiments, having a total volume of less than about 20 ml, or less than about 5 mL.

[47.] A kit comprising:
a first package comprising microparticles comprising an active pharmaceutical ingredient and a polymer, wherein the surface of the microparticles are hydrophilic;
a second vial comprising a hydrophilic, liquid carrier vehicle; and
instructions or printed indicia;
wherein the microparticles are substantially miscible to dispersible in the liquid carrier vehicle.

[48.] A kit comprising:
a first vial comprising microparticles comprising an active pharmaceutical ingredient and a polymer, wherein the surface of the microparticles are hydrophobic;
a second vial comprising a hydrophobic, liquid carrier vehicle; and instructions or printed indicia; wherein the microparticles are substantially miscible to dispersible in the liquid carrier vehicle.

[49.] The kit of any of the above embodiments, wherein the instructions or printed indicia provide for a directions for reconstituting, which include contacting the contents of the first vial with the contents of the second vial, thereby providing a reconstituted composition that is injectable and flowable.

[50.] The kit of any of the above embodiments, wherein the microparticles were previously lyophilized.

[51.] The kit of any of the above embodiments, wherein the instructions on printed indicia instruct injection into at least one of fatty tissue, hydrophobic tissue, and epidural tissue.

[52.] The kit of any of the above embodiments, wherein the instructions on printed indicia instruct injection into at least one of hydrophilic tissues, an eye, vitreous fluid, a joint, and the synovial cavity of a joint.

[53.] The kit of any of the above embodiments, further comprising a hypodermic needle or other delivery device.

[54.] A method comprising administering to a mammal (e.g., human), via injection, the injectable, flowable composition of any of the above embodiments.

[55.] The method of any of the above embodiments, wherein the injectable, flowable composition has a substantially first order release profile.

[56.] The method of any of the above embodiments, wherein the injectable, flowable composition has a substantially zero order release profile.

[57.] The method of any of the above embodiments, wherein when (i) the surface of the microparticles are hydrophilic, and (ii) the liquid carrier vehicle is hydrophilic, then the injectable, flowable composition is injected into a hydrophobic environment.

[58.] The method of any of the above embodiments, wherein when (i) the surface of the microparticles are hydrophilic, and (ii) the liquid carrier vehicle is hydrophilic, then the injectable, flowable composition is injected into fatty tissue.

[59.] The method of any of the above embodiments, wherein when (i) the surface of the microparticles are hydrophilic, and (ii) the liquid carrier vehicle is hydrophilic, then the injectable, flowable composition is injected into an epidural space.

[60.] The method of any of the above embodiments, wherein when (i) the surface of the microparticles are hydrophobic, and (ii) the liquid carrier vehicle is hydrophobic, then the injectable, flowable composition is injected into a hydrophilic environment.

[61.] The method of any of the above embodiments, wherein when (i) the surface of the microparticles are hydrophobic, and (ii) the liquid carrier vehicle is hydrophobic, then the injectable, flowable composition is injected into an eye, or surrounding tissue.

[62.] The method of any of the above embodiments, wherein when (i) the surface of the microparticles are hydrophobic, and (ii) the liquid carrier vehicle is hydrophobic, then the injectable, flowable composition is injected, via an intravitreal injection, into the eye.

[63.] The method of any of the above embodiments, wherein when (i) the surface of the microparticles are hydrophobic, and (ii) the liquid carrier vehicle is hydrophobic, then the injectable, flowable composition is injected into a joint.

[63.] The method of any of the above embodiments, wherein when (i) the surface of the microparticles are hydrophobic, and (ii) the liquid carrier vehicle is hydrophobic, then the injectable, flowable composition is injected into the synovial cavity of a joint.

[65.] The method of any of the above embodiments, for the treatment of pain.

[66.] The method of any of the above embodiments, for the treatment of chronic pain.

[67.] The method of any of the above embodiments, for the treatment of mild pain.

[68.] The method of any of the above embodiments, for the treatment of moderate pain.

[69.] The method of any of the above embodiments, for the treatment of severe pain.

[70.] The method of any of the above embodiments, for the treatment of acute pain.

[71.] The method of any of the above embodiments, for the treatment of neuropathic pain.

[72.] The method of any of the above embodiments, for the treatment of lower back pain.

[73.] The method of any of the above embodiments, for the treatment of sciatica.

[74.] The method of any of the above embodiments, for the treatment of radiculopathy.

[75.] The method of any of the above embodiments, for the treatment of lumbrosacral radiculopathy.

[76.] The method of any one of the above embodiments, wherein the administration is not intradermal or subcutaneous.

[77.] The method of any one of the above embodiments, wherein the administration is epidural.

[78.] The method of any one of the above embodiments [60]-[62], wherein the administration is carried out for the treatment of macular degeneration, or for the treatment of diabetic macular edema.

[79.] The method of any one of the above embodiments, wherein the administration is carried out no more than once per about 12 weeks.

[80.] The method of any one of the above embodiments, wherein the administration is carried out no more than once per about 24 weeks.

[81.] The method of any one of the above embodiments, wherein the administration is carried out with fluoroscopy.

[82.] The method of any one of the above embodiments, wherein the administration is carried out without fluoroscopy.

EXAMPLES

The following illustrative examples are provided to facilitate testing, determine effective dosing, and describe preferred methods for use of the pharmaceutical compositions described herein. The examples below are non-limiting with respect to the claims.

Materials and Methods

To facilitate accurate dosing, the amount of API present in a sample of biodegradable microparticles can be determined. In one approach, a sample of microparticles of the type described herein can be dissolved in an appropriate solvent to form a mixture; the mixture can then be analyzed by known analytical techniques, such as high-performance liquid chromatography (HPLC) and comparing results to those of known reference standards. Other analytical techniques can be used, e.g., spectroscopic analysis.

In-vitro elution of the API from the microparticles can be determined by adding a known amount of the microparticles to 5 mL phosphate buffered saline (PBS) solution at a pH 7.4, and maintaining a constant temperature of 37° C. At selected time intervals, a 2 mL aliquot can be withdrawn through a 0.4 μm filter for analysis; the amount of the aliquot withdrawn can be replenished with an equal amount of preheated PBS. The concentration of the API in the aliquot can be determined according to known methods such as HPLC. Sampling intervals can be adjusted to maintain drug concentration below sink conditions in the test vials.

In one approach, particle size distribution of the various microparticle formulations can be determined by laser diffraction and characterized by scanning electron microscopy. The stability of a suspension of microparticles within a carrier vehicle can be determined by observing settling times. These data can be confirmed by assaying aliquots from top, middle, and bottom locations of the suspension at selected time intervals, e.g., 1 hour, 5 hours, 24 hours, etc.

Synthesis of Microparticles and Testing of Dosage Forms

Procedure [A1]: Microparticle Having a Hydrophilic Surface Created by Block Copolymer-Aqueous Vehicle In this example, microparticles containing an active API can be prepared using the following oil in water emulsion technique. First, an oil phase can be prepared by dissolving dexamethasone acetate and PEG-block-PLGA (mPEG 5000 initiated PLGA with 75/25 lactic acid/glycolic acid molar ratio) in dichloromethane. A water phase can be prepared by dissolving hydrolyzed polyvinyl alcohol (PVA) in deionized water. The deionized water can be saturated with dichloromethane and dexamethasone acetate. Next, the oil phase can be added to the water phase and an emulsion can be formed by agitating with a high-shear rotary immersion mixer. The resulting oil-in-water emulsion can be further processed through a high-shear microfluidizer to reduce the oil droplet size, then stirred to allow the PEG chains to orientate to the oil droplet surface. The resulting emulsion can be added to an excess of deionized water and continuously agitated to harden the polymeric microparticles. Next, after about 60 minutes, the resulting microparticles can be progressively isolated through 50 μm, 10 μm, and 1 μm filters. The particles collected on the 1 micron filter can be washed with deionized water, lyophilized, and stored in sealed containers under refrigeration for further analysis. Sealed vials can be gamma-irradiated prior to analysis or administration.

Procedure [A2]: Microparticle Having a Hydrophilic Surface Created by Block Copolymer-Aqueous Vehicle One alternative approach includes the steps above of Procedure A1, but additional PLGA is added to the oil phase with the dexaemethasone acetate and PEG-block-PLGA. This reduces the overall PEG content of the resulting microparticle.

Procedure [A3]: Microparticle Having a Hydrophilic Surface Created by Block Copolymer-Aqueous Vehicle One alternative approach includes the steps above of Procedure A1, but the emulsion is not microfluidized, and the hardened microparticles can be progressively isolated through 100 μm and 20 μm filters.

Without wishing to be bound by theory, it is believed that the block copolymer PEG-co-PLGA may associate with several surfaces or interfaces: a) the surface of the oil phase droplets in the emulsion acting as a surfactant; b) the hydrophobic blocks with the oil phase; and c) the hydrophilic PEG blocks with the surrounding water phase. Upon hardening, the surface of the microparticles may include PEG-co-PLGA on the surface.

Microparticles prepared according to Procedure [A1] above can be predicted to have an average diameter of about 5 μm and a maximum diameter of about 9 μm. Microparticles prepared according to procedure A3 above can be predicted to have an average diameter of about 40 μm and a maximum diameter of about 100 μm.

In general, without wishing to be bound by theory, the percent-by-weight (% weight) of active API contained within microparticles prepared by the above methods can be approximately equal to, or slightly less than the % weight of the agent with respect to the oil-phase polymer. In the above examples, dexamethasone acetate can be estimated to be 25% by weight of the microparticle. It will be understood that the amount of API contained in the microparticle can be adjusted by varying the drug to polymer ratio in the oil phase. In addition, the API may be incorporated into the oil phase as a suspension if a solvent is used that solublizes the polymer, but not the agent.

Microparticles prepared according to the above steps can be expected to form a stable suspension in water over a reasonable range of solid content, e.g., 1-30% solid content. Such suspension can be stable for greater than 2 hours, which is typically long enough to enable a physician or other practitioner to form and administer the suspension into a patient.

Without wishing to be bound by theory, it can be reasonably expected that dexamethasone acetate will release continuously over 12 weeks in-vitro, with about 10% of the drug released in 3 days, 25% in 25 days, and 40% in 70 days. It will be understood that the release profile may be adjusted by one or more of the following, including combinations: increasing or decreasing drug to polymer ratio; increasing or decreasing polymer molecular weight; increasing or decreasing particle size; increasing or decreasing polymer degradation time (by decreasing or increasing glycolic acid content); or increasing or decreasing hydrophilicity of microparticle surface.

In-Vivo Studies

Epidural Administration in Canine Subjects Using Fluoroscopically-Guided Injection This exemplary approach is a modified version of that described by Cohen (vide supra). Male and female beagles can be acclimated and subjected to baseline neurologic and clinical chemistry examinations. Prior to treatment dogs can be anesthetized with propofol. The injection site can be shaved, and a 19-gauge epidural Touhy needle can be inserted at the L6-7 or L7-S1 interspace. A 22-gauge catheter can be threaded 8-10 cm to approximately the L2-L3 level. The position of the catheter can be verified by injection of contrast media under fluoroscopy. Two (2) mL of an aqueous suspension of microparticles, prepared according to procedure A1 above, can be injected over a period of about 2 minutes. After about 10 minutes the catheter can be removed. Before and after surgery, subject baseline measurements can be obtained, including, for example, temperature and specific behavioral measures (pain tolerance, reflex, mobility, etc.). Before injection, and every 2 days after injection for 84 days, heart rate, blood pressure in the tail, spinal reflexes, sensory and pain responses, proprioception, gait and movement, cranial nerve function, and fundoscopic examination data can be recorded to observe the safety of the injected pharmaceutical composition. Blood samples can be collected prior to injection, then at 1, 2, 4, 8, 24, and 72 hour intervals after injection, and every 7 days thereafter to analyze for the pharmaceutical agent and its metabolized forms. At scheduled intervals, necropsy and histopathology can be performed as described by Cohen, vide supra, in a sub-set of animals.

Without wishing to be bound by theory, pharmaceutical compositions of the type described herein are not expected to elicit any significant or appreciable degree of inflammatory response or cause necrosis. Histological examination may reveal the microparticles to be localized and agglomerated within the epidural space at the site of injection with no evidence of the presence of the injection vehicle after 2 about days. Contents of the treated epidural pocket can be recovered by dissection. The injected microparticles can be isolated from epidural tissue and assayed for drug concentration to determine an in-vivo elution profile. It can be reasonably expected that dexamethasone acetate will be released continuously over 12 weeks, with about 20% of the drug released in 3 days, 50% in 25 days, and 80% in 70 days, with complete microparticle polymer degradation in about 16 weeks.

As described above, pharmaceutical compositions of the type described herein can be used to reduce the risk of medical complications stemming from infarct. Canines can be prepared for treatment as described above. A targeted injection location for the microparticles can be verified with contrast media prior to administration. Three dogs can be given a 2 mL injection of a pharmaceutical composition prepared by procedure A1 above, directly into an artery that passes through the epidural space and 3 dogs can be given an injection of a pharmaceutical composition of the type described herein where the microparticles have an average size larger than 10 μm. For example, a pharmaceutical composition prepared by procedure A3, above, can be used. Before and every 2 hours after each injection, heart rate, blood pressure in the tail, spinal reflexes, sensory and pain responses, proprioception, gait and movement, and cranial nerve function, can be measured. After 24 hours, necropsy/histopathology can be performed as described above to determine the degree of infarct, if any, present in subjects injected with the larger microparticle composition.

It can be reasonably expected that animals injected with microparticles having an average size of less than 10 μm will not show a difference in behavior or vitality over the 24 hour period, nor will their vital signs change drastically. Histological examination of the injected and distal arteries is not expected to reveal evidence of thrombus formation, vessel inflammation, or clotting. In contrast, animals injected with the larger microparticle composition may exhibit signs of paralysis. Histological examination of the injected and distal arteries may reveal severe clotting in distal arteries that supply blood to the spinal cord.

Formula [B]: Microparticles Having a Hydrophobic Surface—Oil Based Vehicle

Microparticles can be prepared by the oil in water emulsion technique. An oil phase can be prepared by dissolving dexamethasone acetate and 75/25 poly-lactic-co-glycolic acid in dichloromethane. A water phase can be prepared by dissolving polyvinyl alcohol in deionized water. The deionized water can then be saturated with dichloromethane and dexamethasone acetate. The oil phase can be added to the water phase with agitation with a high shear rotary immersion mixer to form an emulsion. The resulting oil-in-water emulsion can be further processed through a high shear microfluidizer to reduce the oil droplet size. The resulting emulsion can be added to an excess of deionized water and continuously agitated to harden the polymeric microparticles. After 60 minutes, the resulting microparticles can be isolated through 50 μm, 10 μm, and 1 μm filters. The particles collected on the 1 micron filter can be washed with deionized water, lyophilized, and then stored in sealed containers under refrigeration for further analysis. Sealed vials can be gamma-irradiated prior to analysis or administration.

Injectable suspensions of Formulation [B] can be prepared in water (sterile water for injection) and in silicone oil. Particles are expected to settle in less than 1 hour in water but to remain as a stable suspension in silicone oil. The silicone oil is not expected to dissolve the polymeric microparticles.

Intravitreal Injections in Rabbit

Anesthetized New Zealand Dutch Belted rabbits can be used in this study; topical antibiotic drops can be applied to the treated eyes, and 0.1 mL of Formula [B] can be injected via a 25 gauge needle into the vitreous body in either an aqueous vehicle, [C-a] or silicone oil [C-s]. Prior to treatment, baseline fundus photos can be taken and an ophthalmic examination can be performed. At scheduled times, animals can be euthanized and the vitreous body of the treated eyes removed by dissection. The microparticles can be isolated from the vitreous fluid. Drug content of vitreous fluid and isolated microparticles can be assayed using techniques known in the art. In a second rabbit population, whole eyes can be enucleated and frozen. Cryomicrotome sections can be taken of the frozen eyes to determine location and size domain of injection contents.

The microparticles from the [C-a] injection are expected to be dispersed in various regions of the vitreous after 7 days. In contrast, the microparticles from the [C-s] formulation are expected to be found localized at the site of injection for over 60 days.

All publications, patents, and patent applications are incorporated herein by reference. While in the foregoing specification this invention has been described in relation to certain specific embodiments thereof, and many details have been set forth for purposes of illustration, it will be apparent to those skilled in the art that the present invention is susceptible to additional embodiments, and that certain of the details described herein may be varied considerably without departing from the basic principles of the present invention.

The invention claimed is:

1. A kit comprising:
(a) a first container comprising microparticles comprising an active pharmaceutical ingredient agent and at least one polymer, wherein the microparticles have a $d_{90}$ of less than about 7 μm wherein at least one polymer comprises a block copolymer comprising a polyethylene glycol (PEG) block, and the active pharmaceutical ingredient agent is present in a weight of up to about 40% the weight of the total polymer; and
(b) a second container comprising a carrier vehicle.

2. The kit of claim 1, wherein the microparticles are at least one of biodegradable, bioerodible, and biocompatible.

3. The kit of claim 1, wherein the block copolymer further comprises a poly(lactide), poly(glycolide), poly(caprolactone), poly(valerolactone), or poly(hydroxybutyrate) block.

4. The kit of claim 1, wherein the block copolymer comprises poly-lactide-coglycolide (PLGA) block.

5. The kit of claim 1, wherein the composition formed by combining the contents of the first container with the contents of the second container is at least one of injectable and flowable.

6. The kit of claim 1, wherein the carrier vehicle is a liquid carrier vehicle.

7. The kit of claim 1, wherein the liquid carrier vehicle comprises an aqueous liquid.

8. The kit of claim 1, wherein the composition formed by combining the contents of the first container with the contents of the second container has a total volume of less than about 20 mL.

9. The kit of claim 1, wherein the microparticles are present in a concentration of about 1 mg/mL to about 500 mg/mL in the carrier vehicle.

10. The kit of claim 1, wherein the active pharmaceutical ingredient agent is present in a weight of at least about 10% the weight of the total polymer.

11. The kit of claim 1, wherein the active pharmaceutical ingredient agent is an anti-inflammatory agent.

12. The kit of claim 11, wherein the active pharmaceutical ingredient agent is a synthetic glucocorticoid steroid.

13. The kit of claim 1, wherein the active pharmaceutical ingredient agent is present in a weight of about 20-30% the weight of the total polymer.

14. The kit of claim 1, wherein the microparticles have a $d_{90}$ of greater than 1 μm and less than about 7 μm.

15. The kit of claim 1, wherein the microparticles have a $d_{90}$ of less than about 5 μm.

16. The kit of claim 15, wherein the microparticles have a $d_{90}$ of greater than 1 μm and less than about 5 μm.

\* \* \* \* \*